United States Patent [19]

Knollmueller

[11] 3,960,913

[45] June 1, 1976

[54] HALOGENATED ALKOXYSILANE INTERMEDIATE COMPOUNDS AND THEIR PREPARATION

[75] Inventor: Karl O. Knollmueller, Hamden, Conn.

[73] Assignee: Olin Corporation, New Haven, Conn.

[22] Filed: Sept. 24, 1975

[21] Appl. No.: 616,437

[52] U.S. Cl. .............................. 260/448.8 R; 252/78
[51] Int. Cl.$^2$ ......................... C07F 7/04; C07F 7/18
[58] Field of Search ............................. 260/448.8 R

[56] References Cited
UNITED STATES PATENTS

| | | | |
|---|---|---|---|
| 2,910,496 | 10/1959 | Bailey et al. | 260/448.8 R |
| 2,995,591 | 8/1961 | Kovacich et al. | 260/448.8 R |
| 2,995,592 | 8/1961 | Peeler et al. | 260/448.8 R |
| 3,122,579 | 2/1964 | Leitheiser | 260/448.8 R X |
| 3,541,126 | 11/1970 | Baronnier et al. | 260/448.8 R |

*Primary Examiner*—Paul F. Shaver
*Attorney, Agent, or Firm*—Kenneth P. Glynn

[57] ABSTRACT

Halogenated alkoxysilane intermediate compounds are described having the formula $RSi[OSi(OR')_3]_2X$ wherein X is a halogen, R is hydrogen, an alkyl, alkenyl, aryl or aralkyl group and each R' is independently selected from the same group as R with the proviso that at least a majority of R' radicals are sterically hindered alkyl groups having at least 3 carbon atoms. The preparation of these compounds is also described.

15 Claims, No Drawings

HALOGENATED ALKOXYSILANE INTERMEDIATE COMPOUNDS AND THEIR PREPARATION

The present invention is directed to halogenated oxysilane compounds and their preparation. More particularly, the present invention is directed to halogenated alkoxysilane compounds, and their preparation, the compounds having the general formula:

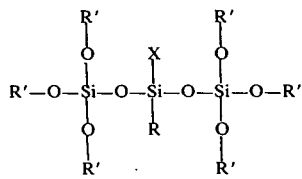 (I)

wherein X is a halogen, R is hydrogen, an alkyl, alkenyl, aryl or aralkyl and each R' is independently selected from the same group as R with the proviso that at least a majority of R' radicals are sterically hindered alkyl groups having at least 3 carbon atoms. This general formula (I) may also be written in an abbreviated form as RSi[OSi(OR')$_3$]$_2$X wherein X, R and R' are as defined.

Silicate esters, silanes, silanols, oxysilanes and oxysilanols are well known for their utility as functional fluids and many of these compounds have been proposed for use as heat transfer fluids, hydraulic fluids, brake fluids, transmission fluids and the like. Halogenated alkoxysilane compounds are now described which may be used as intermediate compounds in the preparation of various novel alkoxysilane and alkoxysilanol compounds having desirable functional fluid properties and more fully described in co-pending U.S. patent applications Ser. Nos. 616,438 and 616,439, filed contemporaneously herewith by the present inventor. The disclosures of these two co-pending applications entitled "Alkoxysilane Cluster Compounds and Their Preparation" and "Alkoxysilanol Compounds and Their Preparation" respectively, are incorporated herein by reference. The intermediate compounds of the present invention are halogenated alkoxysilane compounds which are silicon-oxygen balanced compounds of Formula (I) shown above. Morgan et al. in *The Journal of The American Chemical Society*, Vol. 73, pages 5193–5 (1951), described compounds which are believed to be the closest prior art compounds to the type of cluster compounds which may be prepared by the intermediate compounds of the present invention, but the Morgan et al. compounds differ in that they are centered with a silicon atom completely enclosed by oxygen atoms.

As mentioned, the compounds of the present invention are those represented by the Formula (I) above wherein X is a halogen. The halogen may be F, Cl, Br or I and is desirably Cl, Br or I and preferably Cl. The substituent R shown in Formula (I) is hydrogen, an alkyl, alkenyl, aryl or aralkyl. Desirably, R is hydrogen, an alkyl or alkenyl having about 1 to about 18 carbon atoms or an aryl or aralkyl having about 6 to about 24 carbon atoms. Preferably, R is hydrogen, an alkyl having about 1 to about 8 carbon atoms or an aryl or aralkyl having about 6 to about 14 carbon atoms. In Formula (I), each R' is independently selected from the same group as R, with the proviso that at least a majority of the R' radicals are sterically hindered alkyl groups having at least 3 carbon atoms. The desired and preferred groups for R' are the same as for R subject to the preceding proviso. Desirably, at least a majority of the R' radicals are sterically hindered alkyl groups having about 3 to about 24 carbon atoms and preferably about 4 to about 12 carbon atoms. By sterically hindered alkyl groups is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered alkyl groups include sec. butyl, isobutyl, 2-ethyl butyl, 2-ethyl pentyl, 3-ethyl pentyl, 2-ethyl hexyl, 3-ethyl hexyl, and 2,4-dimethyl-3-pentyl, etc.

In the method of preparing the halogenated alkoxysilane intermediate compounds of the present invention, a trihalosilane is reacted with a trialkoxysilanol in the presence of a hydrogen halide acceptor base and optionally a solvent.

The trihalosilane used in the method of preparing the compounds of the present invention is a substituted trihalosilane of the formula:

R—SiX$_3$ (II)

wherein X and R are defined above.

The trihalosilane of Formula (II) above is reacted with a trialkoxysilanol with sterically hindered alkoxy groups and is represented by the formula:

HOSi(OR')$_3$ (III)

wherein R' is defined above.

The trihalosilane and trialkoxysilanol are reacted in the presence of a hydrogen halide acceptor base compound. The acceptor may be any compound which will accept hydrogen halide and thereby promote the formation of the intermediate compounds of the present invention pursuant to the equation shown below. Among the preferred acceptors are the nitrogenated tertiary organic base compounds having at least 3 carbon atoms, e.g., the lower alkyl and aryl tertiary amines such as triethyl amine, tributyl amine, as well as pyridine, substituted pyridine, N,N'-dimethylaniline, etc.

The reaction which occurs during the formation of the compounds of the present invention using the above reactants may be represented by the following equation:

R—SiX$_3$ + 2HOSi(OR')$_3$ + 2Z $\xrightarrow{\text{Solvent}}$ R—Si[OSi(OR')$_3$]$_2$ + 2Z.HX (A)
$\quad\quad\quad\quad\quad\quad\quad\quad\quad\quad\quad\quad\quad\quad\quad\quad$ |
$\quad\quad\quad\quad\quad\quad\quad\quad\quad\quad\quad\quad\quad\quad\quad\quad$ X wherein Z is the hydrogen halide acceptor base, and the other reactants are described above, and the product is the halogenated alkoxysilane of the present invention.

The above equation (A) suggests that the principal reaction in the method of preparing the compounds of the present invention be carried out in a solvent. While the solvent is not necessary, it does serve to moderate the rate of reaction and thereby to ultimately enhance the separation of the acceptor Z-hydrogen halide HX from the compound product. The solvent used may be any nonprotonic solvent which dissolves the reactants and does not interfere with the Equation(A) reaction. Among the solvents which may be used are benzene, toluene, xylene, high boiling petroleum ether, other ethers such as tetrahydrofurane, and the like.

In reacting the above constituents according to the method of the present invention, in general about 1.5 to about 4 and preferably about 1.8 to about 2.5 moles of the trialkoxysilanol is used per mole of trihalosilane. The hydrogen halide acceptor base is advantageously used in a stoichiometric amount based on the amount of trihalosilane used, e.g., about 2 moles of acceptor per mole of trihalosilane. In general, about 1.5 to about 4 moles, and preferably about 1.8 to about 2.5 moles of the acceptor is used per mole of trihalosilane. The total solvent used in the reaction is a matter of choice and not critical to the reaction, although good results are achieved when about 20 moles to about 80 moles, and preferably about 40 to about 60 moles of solvent is used per mole of trihalosilane. In general, about 0.3 to about 6 parts of solvent per part by weight of total reactants, and preferably about 1 to about 6 parts of solvent per part by weight of total reactants, may be used.

The reactants shown in Equation (A) above react in a very short period of time and a significant amount of reaction product is obtained in a matter of minutes. Because the reaction occurs in most cases in such a short period of time and because the product obtained may be stored in the reaction mixture for long periods of time, there is no criticality to the residence time involved in the reaction. However, for economical commercial production, the reaction may be permitted to proceed so that a substantial amount of the desired intermediate compound is obtained, e.g., for at least about 20 minutes. Desirably, the above reaction may economically be permitted to proceed for at least about ½ hour to about 24 hours or even longer; preferably for about 2 hours to about 12 hours to obtain a commercially useful yield. The intermediate compound-containing reaction mixture may subsequently be used in mixture form or may be subjected to purification and separation techniques.

The reaction represented by Equation (A) may be performed at very low temperatures, room temperature, or even very high temperatures as long as there is no detrimental effect on the reactants or products. Thus, the reaction may be carried out at $-30°C$ up to the reflux temperature of the lowest boiling constituent, but it is preferably carried out at about $0°C$ to about $100°C$. In a preferred batch method embodiment, the reaction is started at a low temperature, e.g., between $-10°C$ and $20°C$, to minimize losses of volatile trihalosilanes and is completed at a higher temperature to drive the intermediate compound-producing reaction as far as possible to completion. Of course, a continuous operation may be employed with a series of reactors in which the first reactor is maintained at the lower temperature and each subsequent reactor is incrimentally higher in temperature to drive the intermediate compound-producing reaction to completion. In any event, the halogenated alkoxysilane compounds may be stored in the reaction mixture or may be separated from the product mixture by filtrations, distillations or other conventional separation techniques, and the particular separation system chosen merely depends upon the desired purity of the final product and its ultimate utility.

The halogenated alkoxysilane compounds, as mentioned, may be used as intermediates in the production of silane and silanol functional fluids such as are described in the above-mentioned co-pending applications, as well as in the preparation of other useful silane-containing products.

As an illustration of the utility of the compounds of the present invention, a halogenated alkoxysilane compound of the present invention may be reacted with water and converted to an alkoxysilanol cluster compound according to the following equation:

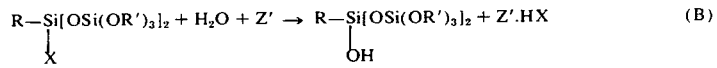

$$R-\underset{X}{Si}[OSi(OR')_3]_2 + H_2O + Z' \rightarrow R-\underset{OH}{Si}[OSi(OR')_3]_2 + Z'.HX \qquad (B)$$

wherein $Z'$ may be any base defined by Z above, or $Z'$ may be an inorganic acceptor base which is water soluble. When the acceptor base is one which is water soluble, a two-phase reaction mixture system may advantageously occur due to the excess water. Acceptable inorganic water soluble bases include $NaHCO_3$, $Na_2CO_3$, buffers such as $NaOOCCH_3$, and the like. By using a water soluble acceptor base to carry out the reaction according to Equation (B) wherein the alkoxysilanol cluster compounds are obtained, cleavage of some of the $OR'$ groups is avoided both in the organic solvent and the water added thereto. In general, at least about 0.8 moles of water per mole of intermediate compound is added and there is no upper limit to the amount of water employed except limitations inherent in commercialization of the method. As a practical matter, about 0.8 to about 500 moles, or even more, of water is used and preferably about 1 to about 100 moles is used, per mole of intermediate compound. The additional acceptor base $Z'$ may be added so that the total amount of acceptor base present will be about 0.7 to about 5 moles and preferably about 0.9 to about 1.5 moles, per mole of intermediate compound.

The cluster compounds obtained are those represented by the product of Equation (B) above and contan an adequate number of silicon atoms to produce good lubricating properties without the need to add lubricity improvers. Additionally, the silicon atoms are adequately shielded by the significant number of sterically hindered alkyl groups having at least 3 carbon atoms and this assures protection against attack by water. Thus, the cluster compounds obtained have been found to have good hydrolytic stability, good lubricating properties and low ASTM viscosity indices with many having pour points below $-40°C$.

The following examples illustrate various embodiments of the present invention, but the present invention should not be construed to be limited thereto:

EXAMPLE 1

A one-liter flask is equipped with a heater, stirrer, reflux condenser, thermometer and equilibrated dropping funnel. To prevent moisture from entering, the reflux condenser is topped with a $CaCl_2$ tube while a slow stream of dry nitrogen is passed through the apparatus via the equilibrated dropping funnel. The flask is charged with 142.3 grams (0.538 moles) of a trialkoxysilanol having the formula $HOSi(OC_4H_9 \text{ sec.})_3$, 42.6 grams (0.538 moles) of pyridine as the acceptor base and 300 ml. of benzene solvent. A solution of 40.2 grams (0.269 moles) of a trihalosilane having the formula $CH_3SiCl_3$ in 90 ml. of benzene is placed into the dropping funnel. The flask contents are set at an initial temperature of 15°C and the trihalosilane solution is added dropwise at such a rate as to maintain the initial temperature of 15°C. After the addition is completed, the contents of the flask are stirred without cooling for about 30 minutes and are then heated to 55°C and maintained at that temperature for about 5 hours. The contents of the flask are then allowed to cool to room temperature and allowed to stand for about 12 hours.

The product mixture contains about 110 grams of a halogenated alkoxysilane compound of the present invention having a boiling point of about 152° ± 1°C at 0.01 mm Hg and having the formula: $CH_3Si[OSi(OC_4H_9 \text{ sec.})_3]_2Cl$.

EXAMPLE 2

The procedure of Example 1 is repeated with the following constituents and amounts:

247.5 grams (0.936 moles) of $HOSi(OC_4H_9 \text{ sec.})_3$;
74.1 grams (0.936 moles) of pyridine in 400 ml of benzene;
98.9 grams (0.468 moles) of $C_6H_5SiCl_3$ in 100 ml of benzene.

The reaction is initially carried out at 10°C and then completed at 55°C for 12 hours. The resulting product mixture contains about 205 grams of a chlorinated alkoxysilane compound having a boiling point of about 175° ± 1°C at about 0.07 mm Hg and having the formula $C_6H_5Si[OSi(OC_4H_9 \text{ sec.})_3]_2Cl$.

EXAMPLE 3

The procedure of Example 1 is repeated with the following constituents and amounts:

127.5 grams (0.481 moles) of $HOSi(OC_4H_9 \text{ sec.})_3$;
63.1 grams (0.797 moles) of pyridine in 600 ml of benzene;
50 grams (0.236 moles) of a phenyl chlorosilane compound having the formula $C_6H_5SiCl_3$ in 60 ml of benzene.

The initial reaction is carried out at 16°C according to Example 1 and the mixture is subsequently heated at 55°C for about 15 hours. The product mixture obtained contains over 100 grams of a compound of the present invention having the formula: $C_6H_5Si[OS(OC_4H_9 \text{ sec.})_3]_2 Cl$.

EXAMPLE 4

This example illustrates the utility of the compound produced by Example 3. The product mixture obtained in Example 3 is first passed through a filter to remove the pyridine hydrochloride by-product contained therein. Next, the benzene phase filtrate is stirred for one hour with 300 ml of water to hydrolize the Si—Cl bonds to SiOH bonds on the intermediate compound $C_6H_5Si[OSi(OC_4H_9 \text{ sec.})_3]_2Cl$ molecules in the product mixture. Next, the product mixture is washed with water until substantially Cl⁻ free and is then dried over $CaCl_2$ and $MgSO_4$ for 5 hours. The mixture is then filtered and vacuum stripped to yield a crude product mixture of about 153 grams.

Fractionation of the crude product mixture yields 113.2 grams (73.9% yield) of an alkoxysilanol cluster compound having the formula $C_6H_5Si[OSi(OC_4H_9 \text{ sec.})_3]_2 OH$. The compound is found to have a boiling point of about 164°C ± 1.5° at a vacuum of about 0.05 to 0.07 mm Hg. The compound has the generic formula of $C_{30}H_{60}O_9Si_3$; calculated C — 55.5%; H — 9.3%; Si—12.98%; found C—55.51%; H — 9.4% and Si — 12.99%. The OH group is confirmed by IR analysis. The viscosity of the compound is found to be 4095 centistokes at −40°F; 21.12 centistokes at 100°F and 3.71 at 210°F. The ASTM scope is 0.81 and wear scar is 0.76 mm. The percent solids remaining after hydrolysis testing is 0.05%. These physical properties establish that the cluster compound is a very good functional fluid.

EXAMPLE 5

The procedure of Example 1 is repeated except that the following constituents and amounts are used:

104.14 grams (0.394 moles) of $HOSi(OC_4H_9 \text{ sec.})_3$;
43.6 grams (0.55 moles) of pyridine in 400 ml of benzene;
21.2 grams (0.132 moles) of an alkenyl chlorosilane of the formula $C_2H_3SiCl_3$ in 80 ml of benzene.

The initial reaction is carried out at about 6°C for about ½ hour and then the reaction mixture is heated to 55°C and maintained at that temperature for about 12 hours. The product mixture is then allowed to cool to room temperature. The product mixture is found to contain about 40 grams of a compound of the present invention having the formula $C_2H_3Si[OSi(OC_4H_9 \text{ sec.})_3]_2 Cl$.

EXAMPLE 6

The procedure of Example 1 is repeated using the following amounts of constituents:

142.3 grams (0.538 moles) of $HOSi(OC_4H_9 \text{ sec.})_3$;
42.6 grams (0.538 moles) of pyridine in 300 ml of benzene;
40.22 grams (0.269 moles) of $CH_3SiCl_3$ in 80 ml of benzene.

The trialkoxysilanol and the pyridine in benzene solvent are combined and cooled under agitation to about 0° to 5°C. The trichlorosilane is added to the cooled mixture dropwise over a one-hour period. The reaction mixture is then allowed to come to room temperature and is further heated to 80°C and is held at 80°C for about 12 hours. The product-containing reaction mixture is then cooled to room temperature and filtered. A pyridine—HCl precipitate is removed by the filtration and the filtrate is subjected to vacuum stripping for removal of the benzene. The remaining product mixture is mixed with 200 ml of hexane and 100 ml of diethyl ether to take up any remaining pyridine—HCl solids. The turbid solution is stirred for 30 minutes with 2 grams of MgSo₄ and 5 grams of diatomaceous earth to coagulate any residual pyridine-HCl. Upon filtration and vacuum stripping of the solvents, about 156.4 grams of a clear solution is obtained. This product is fractionated and about 110.6 grams of a compound of the present invention having the formula CH₃Si[OSi(OC₄H₉ sec.)₃]₂Cl is obtained at about 152°C ± 1°C and 0.1 mm Hg (yield: 67%).

EXAMPLE 7

The reaction of Example 6 is repeated, using the same equipment but a reversed order of addition.

In the three-neck flask is charged 88.66g (0.593 mole) CH₃SiCl₃ in 500 ml of benzene. In the dropping funnel is charged a mixture of:

313.7 grams (1.186 moles) of HOSi(OC₄H₉ sec.)₃;
93.89 grams (1.186 moles) of pyridine in 200 ml of benzene.

While stirring the CH₃SiCl₃ at −10°C, the silanol/pyridine solution is added slowly. During the last third volume addition, the temperature is allowed to stay around 0°C. The mixture is slowly warmed up and an additional 300 ml of benzene is added to ease stirring of the pyridine-HCl. The reaction mixture is heated to 60°C overnight. Upon filtration, 137 grams (1.186 moles) of pyridine-HCl is obtained. Upon removal of benzene and clarifying the solution with 400 ml of hexane and 200 ml of diethyl ether in the presence of diatomaceous earth and drying agent, there is recovered about 350.5 grams of crude product after filtration and vacuum stripping of solvents. Vacuum fractionation of the crude product in a 12-inch Vigreux column produces about 273.8 grams of a compound of the present invention having the formula CH₃Si[OSi(OC₄H₉ sec.)₃]₂Cl with a 76.3% yield.

What is claimed is:

1. A compound of the formula:

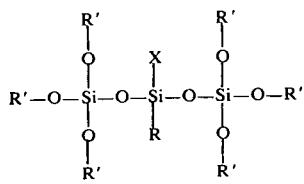

wherein X is a halogen, R is hydrogen, an alkyl, alkenyl, aryl or aralkyl, and each R' is independently selected from the same group as R with the proviso that at least a majority of R' radicals are sterically hindered alkyl groups having at least 3 carbon atoms.

2. The compound of claim 1 wherein R is hydrogen, an alkyl or alkenyl having about 1 to about 18 carbon atoms or an aryl or aralkyl having about 6 to about 24 carbon atoms and wherein each R' is independently selected from the same group as R, subject to the above proviso.

3. The compound of claim 2 wherein X is F, Cl, Br or I and wherein a majority of the R' radicals are sterically hindered alkyl groups having about 3 to about 24 carbon atoms.

4. The compound of claim 1 wherein R is hydrogen, an alkyl having about 1 to about 8 carbon atoms, or an aryl or aralkyl having about 6 to about 14 carbon atoms and wherein each R' is independently selected from the same group as R, subject to the above proviso.

5. The compound of claim 4 wherein X is Cl, Br or I and wherein a majority of the R' radicals are sterically hindered alkyl groups having about 4 to about 12 carbon atoms.

6. The compound of claim 1 wherein a majority of the R' radicals are sterically hindered alkyl groups having about 3 to about 24 carbon atoms.

7. The compound of claim 6 wherein X is Cl and wherein a majority of the R' radicals are sterically hindered alkyl groups having about 4 to about 12 carbon atoms.

8. A method of preparing the compound of claim 1 comprising:
reacting a trihalosilane of the formula:

wherein X and R are defined in claim 1 above;
with about 1.5 to about 4 moles of a trialkoxysilanol per mole of trihalosilane, said trialkoxysilanol having the formula:

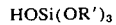

wherein R' is defined in claim 1 above;
in the presence of about 1.5 to about 4 moles of a hydrogen halide acceptor base compound, per mole of trihalosilane to produce a reaction mixture containing the compound of claim 1;
said reaction being carried out at about −30°C to about the reflux temperature of the lowest boiling constituent in the reaction mixture.

9. The method of claim 8 wherein X is F, Cl, Br or I.

10. The method of claim 8 wherein X is Cl, Br or I, wherein R is hydrogen, an alkyl or alkenyl having about 1 to about 18 carbon atoms or an aryl or aralkyl having about 6 to about 24 carbon atoms and wherein each R' is independently selected from the same group as R with the proviso that at least a majority of the R' radicals are sterically hindered alkyl groups having about 3 to about 24 carbon atoms.

11. The method of claim 10 wherein R is hydrogen, an alkyl having about 1 to about 8 carbon atoms or an aryl or aralkyl having about 6 to about 14 carbon atoms and wherein each R' is independently selected from the same group as R, subject to the above proviso.

12. The method of claim 10 wherein X is Cl and wherein a majority of the R' radicals are sterically hindered alkyl groups having about 4 to about 12 carbon atoms.

13. The method of claim 10 wherein about 3 to about 6 moles of the trialkoxysilanol is used per mole of trihalosilane.

14. The method of claim 13 wherein about 3 to about 6 moles of the hydrogen halide acceptor base compound is used per mole of trihalosilane.

15. The method of claim 14 wherein said reaction is carried out at 0°C to 100°C.

* * * * *